United States Patent
Du et al.

(10) Patent No.: US 12,049,488 B2
(45) Date of Patent: Jul. 30, 2024

(54) MODULAR SYNTHETIC RECEPTORS AND METHODS OF USE

(71) Applicant: Lung Biotechnology PBC, Silver Spring, MD (US)

(72) Inventors: Jintang Du, San Diego, CA (US); Nanna Yum, San Diego, CA (US); Michael Brown, San Diego, CA (US); Colin Exline, San Diego, CA (US); Sean Stevens, Del Mar, CA (US)

(73) Assignee: Lung Biotechnology PBC, Silver Spring, MD (US)

( * ) Notice: Subject to any disclaimer, the term of this patent is extended or adjusted under 35 U.S.C. 154(b) by 316 days.

(21) Appl. No.: 17/222,385

(22) Filed: Apr. 5, 2021

(65) Prior Publication Data

US 2021/0317185 A1 Oct. 14, 2021

Related U.S. Application Data

(60) Provisional application No. 63/005,739, filed on Apr. 6, 2020.

(51) Int. Cl.
*C07K 14/705* (2006.01)
*C07K 14/55* (2006.01)
*C07K 16/30* (2006.01)

(52) U.S. Cl.
CPC ........ *C07K 14/70521* (2013.01); *C07K 14/55* (2013.01); *C07K 16/3084* (2013.01); *C07K 2317/622* (2013.01); *C07K 2319/03* (2013.01); *C07K 2319/30* (2013.01)

(58) Field of Classification Search
None
See application file for complete search history.

(56) References Cited

U.S. PATENT DOCUMENTS

| | | | | |
|---|---|---|---|---|
| 2014/0286898 | A1* | 9/2014 | Gavin | C07K 16/00 435/375 |
| 2015/0104450 | A1* | 4/2015 | Minter | A61P 25/00 424/134.1 |
| 2016/0264665 | A1 | 9/2016 | Lim et al. | |
| 2017/0066838 | A1* | 3/2017 | Pulé | C07K 14/7051 |

FOREIGN PATENT DOCUMENTS

WO WO-2016/138034 A1 9/2016
WO WO-2019/141270 A1 7/2019

OTHER PUBLICATIONS

Patel et al. (Frontiers in Immunology Feb. 14, 2019, 10: 223) (Year: 2019).*
Morsut et al., "Engineering Customized Cell Sensing and Response Behaviors Using Synthetic Notch Receptors," Cell, Feb. 11, 2016, 164:780-791.
Morsut et al., "Engineering Customized Cell Sensing and Response Behaviors Using Synthetic Notch Receptors," Cell, Jan. 28, 2016, 164(4):780-791.
Roybal et al., "Engineering T Cells with Customized Therapeutic Response Programs Using Synthetic Notch Receptors," Cell, Sep. 29, 2016, 167(2):419-432.

* cited by examiner

*Primary Examiner* — Peter J Reddig
(74) *Attorney, Agent, or Firm* — Foley & Lardner LLP

(57) ABSTRACT

Modular synthetic receptors are provided. The synthetic receptors may include an extracellular domain capable of binding to one or more ligand molecules and may be released from the synthetic receptor after binding, a transmembrane domain derived from the Notch receptor, and an intracellular domain which may have one or more functional activities when released from the synthetic receptor. A method of use for the synthetic receptors is also provided, wherein upon binding of the extracellular domain to a specific ligand, the synthetic receptor undergoes proteolytic cleavage to release either or both the extracellular and intracellular domains. The extracellular binding domain, if released, may continue to bind to its cognate ligand and may carry one or more additional functional activities and the intracellular domain, if released, may stimulate or inhibit one or more intracellular activities.

16 Claims, 8 Drawing Sheets

Specification includes a Sequence Listing.

```
                          1st cleavage                                              2nd cleavage
dNotch    QRNDFQIHSRGIKNGDEDNGEPPANVKYVIT-----GIIVIIALAFFMVLST--QRKAHG-
GLP-1     GPITEAMVAPKR---NEIDEGWSRSQV-ILFAC-----IAFAPGTVVAVIAKNCERSPKRK
pNotch1   SNIPYKIEAQSE-----TVEPPPPPLHFMYV-A-VVAFVFFV-G-CLLSR---KRCRQ--
mNotch1   SNIPYKIEAKSE-----PVEPPLPSQLHLMYV-A-AAAFVFFV-G-CLLSR---KRCRQ--
hNotch1   SNIPYKIEAQSE-----TVEPPPAQLHFMYV-A-AAAFVFFV-G-CLLSR---KRCRQ--
hNotch2   QGTLSYPLVSVSE-----SLTPERTQL--LYLL-A-VAVVIIFII-L-LIMAK---RKCKHG-
hNotch3   RDFPYPLRDRGE-----PLEPPEPSVPLLPLL-V-AGAVLVIL-V-LMVAR---RKRE---
hNotch4   EPLLPGPLLAHPH-----AGTAPPANQLPWPVLCSVAGVIALGAL-LVLQLIR---RRRE--
```

FIG. 7

SEQUENCE LISTING

```
<160> NUMBER OF SEQ ID NOS: 13

<210> SEQ ID NO 1
<211> LENGTH: 832
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Gly Ser Gln Ile Val Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Ala His Phe Arg Gly Ser Gly Ser Gly Thr Ser Tyr Ser Leu Thr Ile
        195                 200                 205

Ser Gly Met Glu Ala Glu Asp Ala Ala Thr Tyr Tyr Cys Gln Gln Trp
    210                 215                 220

Ser Ser Asn Pro Phe Thr Phe Gly Ser Gly Thr Lys Leu Glu Ile Asn
225                 230                 235                 240
```

```
Arg Ile Leu Asp Tyr Ser Phe Gly Gly Gly Ala Gly Arg Asp Ile Pro
                245             250             255

Pro Pro Leu Ile Glu Glu Ala Cys Glu Leu Pro Glu Cys Gln Glu Asp
                260             265             270

Ala Gly Asn Lys Val Cys Ser Leu Gln Cys Asn Asn His Ala Cys Gly
            275             280             285

Trp Asp Gly Gly Asp Cys Ser Leu Asn Phe Asn Asp Pro Trp Lys Asn
        290             295             300

Cys Thr Gln Ser Leu Gln Cys Trp Lys Tyr Phe Ser Asp Gly His Cys
305             310             315                         320

Asp Ser Gln Cys Asn Ser Ala Gly Cys Leu Phe Asp Gly Phe Asp Cys
                325             330             335

Gln Arg Ala Glu Gly Gln Cys Asn Pro Leu Tyr Asp Gln Tyr Cys Lys
                340             345             350

Asp His Phe Ser Asp Gly His Cys Asp Gln Gly Cys Asn Ser Ala Glu
                355             360             365

Cys Glu Trp Asp Gly Leu Asp Cys Ala Glu His Val Pro Glu Arg Leu
            370             375             380

Ala Ala Gly Thr Leu Val Val Val Val Leu Met Pro Pro Glu Gln Leu
385             390             395             400

Arg Asn Ser Ser Phe His Phe Leu Arg Glu Leu Ser Arg Val Leu His
                405             410             415

Thr Asn Val Val Phe Lys Arg Asp Ala His Gly Gln Gln Met Ile Phe
                420             425             430

Pro Tyr Tyr Gly Arg Glu Glu Leu Arg Lys His Pro Ile Lys Arg
                435             440             445

Ala Ala Glu Gly Trp Ala Ala Pro Asp Ala Leu Leu Gly Gln Val Lys
        450             455             460

Ala Ser Leu Leu Pro Gly Gly Ser Glu Gly Gly Arg Arg Arg Arg Glu
465             470             475             480

Leu Asp Pro Met Asp Val Arg Gly Ser Ile Val Tyr Leu Glu Ile Asp
                485             490             495

Asn Arg Gln Cys Val Gln Ala Ser Ser Gln Cys Phe Gln Ser Ala Thr
                500             505             510

Asp Val Ala Ala Phe Leu Gly Ala Leu Ala Ser Leu Gly Ser Leu Asn
            515             520             525

Ile Pro Tyr Lys Ile Glu Ala Val Gln Ser Glu Thr Val Glu Pro Pro
            530             535             540

Pro Pro Ala Gln Leu His Phe Met Tyr Val Ala Ala Ala Ala Phe Val
545             550             555             560

Leu Leu Phe Phe Val Gly Cys Gly Val Leu Leu Ser Arg Lys Arg Arg
                565             570             575

Arg Gln Leu Cys Ile Gln Lys Leu Met Ser Arg Leu Asp Lys Ser Lys
                580             585             590

Val Ile Asn Ser Ala Leu Glu Leu Asn Glu Val Gly Ile Glu Gly
            595             600             605

Leu Thr Thr Arg Lys Leu Ala Gln Lys Leu Gly Val Glu Gln Pro Thr
        610             615             620

Leu Tyr Trp His Val Lys Asn Lys Arg Ala Leu Leu Asp Ala Leu Ala
625             630             635             640

Ile Glu Met Leu Asp Arg His Thr His Phe Cys Pro Leu Glu Gly
            645             650             655
```

-continued

Glu Ser Trp Gln Asp Phe Leu Arg Asn Asn Ala Lys Ser Phe Arg Cys
           660                 665                 670

Ala Leu Leu Ser His Arg Asp Gly Ala Lys Val His Leu Gly Thr Arg
        675                 680                 685

Pro Thr Glu Lys Gln Tyr Glu Thr Leu Glu Asn Gln Leu Ala Phe Leu
    690                 695                 700

Cys Gln Gln Gly Phe Ser Leu Glu Asn Ala Leu Tyr Ala Leu Ser Ala
705                 710                 715                 720

Val Gly His Phe Thr Leu Gly Cys Val Leu Glu Asp Gln Glu His Gln
                725                 730                 735

Val Ala Lys Glu Glu Arg Glu Thr Pro Thr Thr Asp Ser Met Pro Pro
        740                 745                 750

Leu Leu Arg Gln Ala Ile Glu Leu Phe Asp His Gln Gly Ala Glu Pro
        755                 760                 765

Ala Phe Leu Phe Gly Leu Glu Leu Ile Ile Cys Gly Leu Glu Lys Gln
        770                 775                 780

Leu Lys Cys Glu Ser Gly Gly Pro Ala Asp Ala Leu Asp Asp Phe Asp
785                 790                 795                 800

Leu Asp Met Leu Pro Ala Asp Ala Leu Asp Asp Phe Asp Leu Asp Met
                805                 810                 815

Leu Pro Ala Asp Ala Leu Asp Asp Phe Asp Leu Asp Met Leu Pro Gly
            820                 825                 830

<210> SEQ ID NO 2
<211> LENGTH: 833
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Leu Gln Ser Gly Pro Glu Leu Glu Lys Pro Gly Ala
1               5                   10                  15

Ser Val Met Ile Ser Cys Lys Ala Ser Gly Ser Ser Phe Thr Gly Tyr
            20                  25                  30

Asn Met Asn Trp Val Arg Gln Asn Ile Gly Lys Ser Leu Glu Trp Ile
        35                  40                  45

Gly Ala Ile Asp Pro Tyr Tyr Gly Gly Thr Ser Tyr Asn Gln Lys Phe
    50                  55                  60

Lys Gly Arg Ala Thr Leu Thr Val Asp Lys Ser Ser Ser Thr Ala Tyr
65                  70                  75                  80

Met His Leu Lys Ser Leu Thr Ser Glu Asp Ser Ala Val Tyr Tyr Cys
                85                  90                  95

Val Ser Gly Met Glu Tyr Trp Gly Gln Gly Thr Ser Val Thr Val Ser
            100                 105                 110

Ser Gly Gly Gly Gly Ser Gly Gly Gly Gly Ser Gly Gly Gly Gly Ser
        115                 120                 125

Asp Val Val Met Thr Gln Thr Pro Leu Ser Leu Pro Val Ser Leu Gly
    130                 135                 140

Asp Gln Ala Ser Ile Ser Cys Arg Ser Ser Gln Ser Leu Val His Arg
145                 150                 155                 160

Asn Gly Asn Thr Tyr Leu His Trp Tyr Leu Gln Lys Pro Gly Gln Ser
                165                 170                 175

Pro Lys Leu Leu Ile His Lys Val Ser Asn Arg Phe Ser Gly Val Pro
            180                 185                 190

```
Asp Arg Phe Ser Gly Ser Gly Ser Gly Thr Asp Phe Thr Leu Lys Ile
        195                 200                 205

Ser Arg Val Glu Ala Glu Asp Leu Gly Val Tyr Phe Cys Ser Gln Ser
210                 215                 220

Thr His Val Pro Pro Leu Thr Phe Gly Ala Gly Thr Lys Leu Glu Leu
225                 230                 235                 240

Lys Arg Ile Leu Asp Tyr Ser Phe Gly Gly Ala Gly Arg Asp Ile
        245                 250                 255

Pro Pro Pro Leu Ile Glu Glu Ala Cys Glu Leu Pro Glu Cys Gln Glu
            260                 265                 270

Asp Ala Gly Asn Lys Val Cys Ser Leu Gln Cys Asn Asn His Ala Cys
        275                 280                 285

Gly Trp Asp Gly Gly Asp Cys Ser Leu Asn Phe Asn Asp Pro Trp Lys
    290                 295                 300

Asn Cys Thr Gln Ser Leu Gln Cys Trp Lys Tyr Phe Ser Asp Gly His
305                 310                 315                 320

Cys Asp Ser Gln Cys Asn Ser Ala Gly Cys Leu Phe Asp Gly Phe Asp
                325                 330                 335

Cys Gln Arg Ala Glu Gly Gln Cys Asn Pro Leu Tyr Asp Gln Tyr Cys
            340                 345                 350

Lys Asp His Phe Ser Asp Gly His Cys Asp Gln Gly Cys Asn Ser Ala
        355                 360                 365

Glu Cys Glu Trp Asp Gly Leu Asp Cys Ala Glu His Val Pro Glu Arg
    370                 375                 380

Leu Ala Ala Gly Thr Leu Val Val Val Val Leu Met Pro Pro Glu Gln
385                 390                 395                 400

Leu Arg Asn Ser Ser Phe His Phe Leu Arg Glu Leu Ser Arg Val Leu
                405                 410                 415

His Thr Asn Val Val Phe Lys Arg Asp Ala His Gly Gln Gln Met Ile
                420                 425                 430

Phe Pro Tyr Tyr Gly Arg Glu Glu Leu Arg Lys His Pro Ile Lys
        435                 440                 445

Arg Ala Ala Glu Gly Trp Ala Ala Pro Asp Ala Leu Leu Gly Gln Val
    450                 455                 460

Lys Ala Ser Leu Leu Pro Gly Gly Ser Glu Gly Gly Arg Arg Arg
465                 470                 475                 480

Glu Leu Asp Pro Met Asp Val Arg Gly Ser Ile Val Tyr Leu Glu Ile
            485                 490                 495

Asp Asn Arg Gln Cys Val Gln Ala Ser Ser Gln Cys Phe Gln Ser Ala
        500                 505                 510

Thr Asp Val Ala Ala Phe Leu Gly Ala Leu Ala Ser Leu Gly Ser Leu
        515                 520                 525

Asn Ile Pro Tyr Lys Ile Glu Ala Val Gln Ser Glu Thr Val Glu Pro
530                 535                 540

Pro Pro Pro Ala Gln Leu His Phe Met Tyr Val Ala Ala Ala Ala Phe
545                 550                 555                 560

Val Leu Leu Phe Phe Val Gly Cys Gly Val Leu Leu Ser Arg Lys Arg
                565                 570                 575

Arg Arg Gln Leu Cys Ile Gln Lys Leu Met Ser Arg Leu Asp Lys Ser
            580                 585                 590

Lys Val Ile Asn Ser Ala Leu Glu Leu Leu Asn Glu Val Gly Ile Glu
        595                 600                 605
```

```
Gly Leu Thr Thr Arg Lys Leu Ala Gln Lys Leu Gly Val Glu Gln Pro
    610                 615                 620

Thr Leu Tyr Trp His Val Lys Asn Lys Arg Ala Leu Leu Asp Ala Leu
625                 630                 635                 640

Ala Ile Glu Met Leu Asp Arg His His Thr His Phe Cys Pro Leu Glu
                645                 650                 655

Gly Glu Ser Trp Gln Asp Phe Leu Arg Asn Asn Ala Lys Ser Phe Arg
            660                 665                 670

Cys Ala Leu Leu Ser His Arg Asp Gly Ala Lys Val His Leu Gly Thr
        675                 680                 685

Arg Pro Thr Glu Lys Gln Tyr Glu Thr Leu Glu Asn Gln Leu Ala Phe
    690                 695                 700

Leu Cys Gln Gln Gly Phe Ser Leu Glu Asn Ala Leu Tyr Ala Leu Ser
705                 710                 715                 720

Ala Val Gly His Phe Thr Leu Gly Cys Val Leu Glu Asp Gln Glu His
                725                 730                 735

Gln Val Ala Lys Glu Glu Arg Glu Thr Pro Thr Thr Asp Ser Met Pro
            740                 745                 750

Pro Leu Leu Arg Gln Ala Ile Glu Leu Phe Asp His Gln Gly Ala Glu
        755                 760                 765

Pro Ala Phe Leu Phe Gly Leu Glu Leu Ile Ile Cys Gly Leu Glu Lys
    770                 775                 780

Gln Leu Lys Cys Glu Ser Gly Gly Pro Ala Asp Ala Leu Asp Asp Phe
785                 790                 795                 800

Asp Leu Asp Met Leu Pro Ala Asp Ala Leu Asp Asp Phe Asp Leu Asp
                805                 810                 815

Met Leu Pro Ala Asp Ala Leu Asp Asp Phe Asp Leu Asp Met Leu Pro
            820                 825                 830

Gly

<210> SEQ ID NO 3
<211> LENGTH: 822
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Ser Gly Gly Gly Gly
        115                 120                 125
```

-continued

Ser Gly Gly Gly Gly Ser Gln Ile Val Leu Thr Gln Ser Pro Ala Ile
130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Leu Ala Ser Gly Val Pro
                180                 185                 190

Ala His Phe Arg Gly Ser Gly Ser Gly Thr Ser Tyr Ser Leu Thr Ile
            195                 200                 205

Ser Gly Met Glu Ala Glu Asp Ala Ala Thr Tyr Tyr Cys Gln Gln Trp
210                 215                 220

Ser Ser Asn Pro Phe Thr Phe Gly Ser Gly Thr Lys Leu Glu Ile Asn
225                 230                 235                 240

Arg Ile Leu Asp Tyr Ser Phe Thr Gly Gly Ala Gly Arg Asp Ile Pro
                245                 250                 255

Pro Pro Gln Ile Glu Glu Ala Cys Glu Leu Pro Glu Cys Gln Val Asp
            260                 265                 270

Ala Gly Asn Lys Val Cys Asn Leu Gln Cys Asn Asn His Ala Cys Gly
            275                 280                 285

Trp Asp Gly Gly Asp Cys Ser Leu Asn Phe Asn Asp Pro Trp Lys Asn
290                 295                 300

Cys Thr Gln Ser Leu Gln Cys Trp Lys Tyr Phe Ser Asp Gly His Cys
305                 310                 315                 320

Asp Ser Gln Cys Asn Ser Ala Gly Cys Leu Phe Asp Gly Phe Asp Cys
                325                 330                 335

Gln Leu Thr Glu Gly Gln Cys Asn Pro Leu Tyr Asp Gln Tyr Cys Lys
            340                 345                 350

Asp His Phe Ser Asp Gly His Cys Asp Gln Gly Cys Asn Ser Ala Glu
            355                 360                 365

Cys Glu Trp Asp Gly Leu Asp Cys Ala Glu His Val Pro Glu Arg Leu
370                 375                 380

Ala Ala Gly Thr Leu Val Leu Val Val Leu Leu Pro Pro Asp Gln Leu
385                 390                 395                 400

Arg Asn Asn Ser Phe His Phe Leu Arg Glu Leu Ser His Val Leu His
                405                 410                 415

Thr Asn Val Val Phe Lys Arg Asp Ala Gln Gly Gln Gln Met Ile Phe
            420                 425                 430

Pro Tyr Tyr Gly His Glu Glu Leu Arg Lys His Pro Ile Lys Arg
            435                 440                 445

Ser Thr Val Gly Trp Ala Thr Ser Ser Leu Leu Pro Gly Thr Ser Gly
            450                 455                 460

Gly Arg Gln Arg Arg Glu Leu Asp Pro Met Asp Ile Arg Gly Ser Ile
465                 470                 475                 480

Val Tyr Leu Glu Ile Asp Asn Arg Gln Cys Val Gln Ser Ser Ser Gln
                485                 490                 495

Cys Phe Gln Ser Ala Thr Asp Val Ala Ala Phe Leu Gly Ala Leu Ala
                500                 505                 510

Ser Leu Gly Ser Leu Asn Ile Pro Tyr Lys Ile Glu Ala Val Lys Ser
            515                 520                 525

Glu Pro Val Glu Pro Pro Leu Pro Ser Gln Leu His Leu Met Tyr Val
530                 535                 540

Ala Ala Ala Ala Phe Val Leu Leu Phe Phe Val Gly Cys Gly Val Leu

```
                545                 550                 555                 560
Leu Ser Arg Lys Arg Arg Gln Leu Cys Ile Gln Lys Leu Met Ser
                565                 570                 575

Arg Leu Asp Lys Ser Lys Val Ile Asn Ser Ala Leu Glu Leu Leu Asn
                580                 585                 590

Glu Val Gly Ile Glu Gly Leu Thr Thr Arg Lys Leu Ala Gln Lys Leu
                595                 600                 605

Gly Val Glu Gln Pro Thr Leu Tyr Trp His Val Lys Asn Lys Arg Ala
            610                 615                 620

Leu Leu Asp Ala Leu Ala Ile Glu Met Leu Asp Arg His His Thr His
625                 630                 635                 640

Phe Cys Pro Leu Glu Gly Glu Ser Trp Gln Asp Phe Leu Arg Asn Asn
                645                 650                 655

Ala Lys Ser Phe Arg Cys Ala Leu Leu Ser His Arg Asp Gly Ala Lys
                660                 665                 670

Val His Leu Gly Thr Arg Pro Thr Glu Lys Gln Tyr Glu Thr Leu Glu
            675                 680                 685

Asn Gln Leu Ala Phe Leu Cys Gln Gln Gly Phe Ser Leu Glu Asn Ala
        690                 695                 700

Leu Tyr Ala Leu Ser Ala Val Gly His Phe Thr Leu Gly Cys Val Leu
705                 710                 715                 720

Glu Asp Gln Glu His Gln Val Ala Lys Glu Glu Arg Glu Thr Pro Thr
                725                 730                 735

Thr Asp Ser Met Pro Pro Leu Leu Arg Gln Ala Ile Glu Leu Phe Asp
            740                 745                 750

His Gln Gly Ala Glu Pro Ala Phe Leu Phe Gly Leu Glu Leu Ile Ile
        755                 760                 765

Cys Gly Leu Glu Lys Gln Leu Lys Cys Glu Ser Gly Gly Pro Ala Asp
            770                 775                 780

Ala Leu Asp Asp Phe Asp Leu Asp Met Leu Pro Ala Asp Ala Leu Asp
785                 790                 795                 800

Asp Phe Asp Leu Asp Met Leu Pro Ala Asp Ala Leu Asp Asp Phe Asp
                805                 810                 815

Leu Asp Met Leu Pro Gly
            820

<210> SEQ ID NO 4
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80
```

```
Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Ala Glu Ala Ala Lys Glu Ala Ala
130                 135                 140

Ala Lys Glu Ala Ala Lys Ala Gly Gly Asp Lys Thr His Thr Cys
145                 150                 155                 160

Pro Pro Cys Pro Ala Pro Glu Leu Leu Gly Gly Pro Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
        195                 200                 205

Phe Asn Trp Tyr Val Asp Gly Val Glu Val His Asn Ala Lys Thr Lys
    210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Pro Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Asp Glu Leu Thr Lys Asn Gln Val Ser Leu Thr Cys Leu Val Lys
290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
            340                 345                 350

Gln Gly Asn Val Phe Ser Cys Ser Val Met His Glu Ala Leu His Asn
        355                 360                 365

His Tyr Thr Gln Lys Ser Leu Ser Leu Ser Pro Gly Lys
    370                 375                 380

<210> SEQ ID NO 5
<211> LENGTH: 767
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60
```

```
Gln Tyr Thr Cys His Lys Gly Gly Glu Val Leu Ser His Ser Leu Leu
 65                  70                  75                  80

Leu Leu His Lys Lys Glu Asp Gly Ile Trp Ser Thr Asp Ile Leu Lys
                 85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Ser Gly Gly Ser Gly Gly Ser Gly Gly Ser Gly Gly
305                 310                 315                 320

Gly Ser Arg Asn Leu Pro Val Ala Thr Pro Asp Pro Gly Met Phe Pro
                325                 330                 335

Cys Leu His His Ser Gln Asn Leu Leu Arg Ala Val Ser Asn Met Leu
            340                 345                 350

Gln Lys Ala Arg Gln Thr Leu Glu Phe Tyr Pro Cys Thr Ser Glu Glu
        355                 360                 365

Ile Asp His Glu Asp Ile Thr Lys Asp Lys Thr Ser Thr Val Glu Ala
    370                 375                 380

Cys Leu Pro Leu Glu Leu Thr Lys Asn Glu Ser Cys Leu Asn Ser Arg
385                 390                 395                 400

Glu Thr Ser Phe Ile Thr Asn Gly Ser Cys Leu Ala Ser Arg Lys Thr
                405                 410                 415

Ser Phe Met Met Ala Leu Cys Leu Ser Ser Ile Tyr Glu Asp Leu Lys
            420                 425                 430

Met Tyr Gln Val Glu Phe Lys Thr Met Asn Ala Lys Leu Leu Met Asp
        435                 440                 445

Pro Lys Arg Gln Ile Phe Leu Asp Gln Asn Met Leu Ala Val Ile Asp
    450                 455                 460

Glu Leu Met Gln Ala Leu Asn Phe Asn Ser Glu Thr Val Pro Gln Lys
465                 470                 475                 480
```

```
Ser Ser Leu Glu Glu Pro Asp Phe Tyr Lys Thr Lys Ile Lys Leu Cys
                485                 490                 495

Ile Leu Leu His Ala Phe Arg Ile Arg Ala Val Thr Ile Asp Arg Val
            500                 505                 510

Met Ser Tyr Leu Asn Ala Ser Gly Gly Ala Glu Ala Ala Ala Lys Glu
        515                 520                 525

Ala Ala Ala Lys Glu Ala Ala Ala Lys Ala Gly Gly Asp Lys Thr His
    530                 535                 540

Thr Cys Pro Pro Cys Pro Ala Pro Glu Leu Leu Gly Gly Pro Ser Val
545                 550                 555                 560

Phe Leu Phe Pro Pro Lys Pro Lys Asp Thr Leu Met Ile Ser Arg Thr
                565                 570                 575

Pro Glu Val Thr Cys Val Val Val Asp Val Ser His Glu Asp Pro Glu
            580                 585                 590

Val Lys Phe Asn Trp Tyr Val Asp Gly Val Glu Val His Asn Ala Lys
        595                 600                 605

Thr Lys Pro Arg Glu Glu Gln Tyr Asn Ser Thr Tyr Arg Val Val Ser
    610                 615                 620

Val Leu Thr Val Leu His Gln Asp Trp Leu Asn Gly Lys Glu Tyr Lys
625                 630                 635                 640

Cys Lys Val Ser Asn Lys Ala Leu Pro Ala Pro Ile Glu Lys Thr Ile
                645                 650                 655

Ser Lys Ala Lys Gly Gln Pro Arg Glu Pro Gln Val Tyr Thr Leu Pro
            660                 665                 670

Pro Ser Arg Asp Glu Leu Thr Lys Asn Gln Val Ser Leu Thr Cys Leu
        675                 680                 685

Val Lys Gly Phe Tyr Pro Ser Asp Ile Ala Val Glu Trp Glu Ser Asn
    690                 695                 700

Gly Gln Pro Glu Asn Asn Tyr Lys Thr Thr Pro Pro Val Leu Asp Ser
705                 710                 715                 720

Asp Gly Ser Phe Phe Leu Tyr Ser Lys Leu Thr Val Asp Lys Ser Arg
                725                 730                 735

Trp Gln Gln Gly Asn Val Phe Ser Cys Ser Val Met His Glu Ala Leu
            740                 745                 750

His Asn His Tyr Thr Gln Lys Ser Leu Ser Leu Ser Pro Gly Lys
        755                 760                 765

<210> SEQ ID NO 6
<211> LENGTH: 59
<212> TYPE: PRT
<213> ORGANISM: Drosophila sp.

<400> SEQUENCE: 6

Gln Leu Arg Asn Asp Phe Gln Ile His Ser Val Arg Gly Ile Lys Asn
1               5                   10                  15

Pro Gly Asp Glu Asp Asn Gly Glu Pro Pro Ala Asn Val Lys Tyr Val
            20                  25                  30

Ile Thr Gly Ile Ile Leu Val Ile Ile Ala Leu Ala Phe Phe Gly Met
        35                  40                  45

Val Leu Ser Thr Gln Arg Lys Arg Ala His Gly
    50                  55

<210> SEQ ID NO 7
<211> LENGTH: 58
<212> TYPE: PRT
<213> ORGANISM: Caenorhabditis sp.
```

<400> SEQUENCE: 7

Gly Leu Pro Ile Thr Glu Ala Met Val Ala Val Pro Lys Arg Asn Glu
1               5                   10                  15

Ile Asp Glu Gly Trp Ser Arg Ser Gln Val Ile Leu Phe Ala Cys Ile
            20                  25                  30

Ala Phe Leu Ala Phe Gly Thr Val Val Ala Gly Val Ile Ala Lys Asn
        35                  40                  45

Gly Pro Glu Arg Ser Arg Lys Arg Lys Met
    50                  55

<210> SEQ ID NO 8
<211> LENGTH: 53
<212> TYPE: PRT
<213> ORGANISM: Sus sp.

<400> SEQUENCE: 8

Ser Leu Asn Ile Pro Tyr Lys Ile Glu Ala Val Gln Ser Glu Thr Val
1               5                   10                  15

Glu Pro Pro Pro Pro Pro Leu His Phe Met Tyr Val Ala Val Val
            20                  25                  30

Ala Phe Val Leu Leu Phe Phe Val Gly Cys Gly Val Leu Leu Ser Arg
        35                  40                  45

Lys Arg Arg Arg Gln
    50

<210> SEQ ID NO 9
<211> LENGTH: 53
<212> TYPE: PRT
<213> ORGANISM: Mus sp.

<400> SEQUENCE: 9

Ser Leu Asn Ile Pro Tyr Lys Ile Glu Ala Val Lys Ser Glu Pro Val
1               5                   10                  15

Glu Pro Pro Leu Pro Ser Gln Leu His Leu Met Tyr Val Ala Ala Ala
            20                  25                  30

Ala Phe Val Leu Leu Phe Phe Val Gly Cys Gly Val Leu Leu Ser Arg
        35                  40                  45

Lys Arg Arg Arg Gln
    50

<210> SEQ ID NO 10
<211> LENGTH: 53
<212> TYPE: PRT
<213> ORGANISM: Homo sapiens

<400> SEQUENCE: 10

Ser Leu Asn Ile Pro Tyr Lys Ile Glu Ala Val Gln Ser Glu Thr Val
1               5                   10                  15

Glu Pro Pro Pro Pro Ala Gln Leu His Phe Met Tyr Val Ala Ala Ala
            20                  25                  30

Ala Phe Val Leu Leu Phe Phe Val Gly Cys Gly Val Leu Leu Ser Arg
        35                  40                  45

Lys Arg Arg Arg Gln
    50

<210> SEQ ID NO 11
<211> LENGTH: 52
<212> TYPE: PRT

```
<213> ORGANISM: Homo sapiens

<400> SEQUENCE: 11

Gln Gly Thr Leu Ser Tyr Pro Leu Val Ser Val Val Ser Glu Ser Leu
1               5                   10                  15

Thr Pro Glu Arg Thr Gln Leu Leu Tyr Leu Leu Ala Val Ala Val Val
            20                  25                  30

Ile Ile Leu Phe Ile Ile Leu Leu Gly Val Ile Met Ala Lys Arg Lys
                35                  40                  45

Arg Lys His Gly
        50

<210> SEQ ID NO 12
<211> LENGTH: 52
<212> TYPE: PRT
<213> ORGANISM: Homo sapiens

<400> SEQUENCE: 12

Arg Leu Asp Phe Pro Tyr Pro Leu Arg Asp Val Arg Gly Glu Pro Leu
1               5                   10                  15

Glu Pro Pro Glu Pro Ser Val Pro Leu Leu Pro Leu Leu Val Ala Gly
            20                  25                  30

Ala Val Leu Leu Leu Val Ile Leu Val Leu Gly Val Met Val Ala Arg
                35                  40                  45

Arg Lys Arg Glu
        50

<210> SEQ ID NO 13
<211> LENGTH: 56
<212> TYPE: PRT
<213> ORGANISM: Homo sapiens

<400> SEQUENCE: 13

Glu Pro Leu Leu Pro Gly Pro Leu Leu Ala Val His Pro His Ala Gly
1               5                   10                  15

Thr Ala Pro Pro Ala Asn Gln Leu Pro Trp Pro Val Leu Cys Ser Pro
            20                  25                  30

Val Ala Gly Val Ile Leu Leu Ala Leu Gly Ala Leu Leu Val Leu Gln
                35                  40                  45

Leu Ile Arg Arg Arg Arg Arg Glu
        50              55
```

MODULAR SYNTHETIC RECEPTORS AND METHODS OF USE

CROSS-REFERENCE TO RELATED APPLICATIONS

This application claims priority to U.S. Provisional Application No. 63/005,739, filed Apr. 6, 2020, the entire contents of which are incorporated herein.

SEQUENCE LISTING

The instant application contains a Sequence Listing which has been submitted electronically in ASCII format and is hereby incorporated by reference in its entirety. Said ASCII copy, created on May 27, 2021, is named 080618-2004_SL.txt and is 36,183 bytes in size.

TECHNICAL FIELD

The present application relates to novel receptors, specifically Notch or CTLA-4 synthetic receptors designed for transplantation, oncology, and autoimmune therapies.

BACKGROUND

Mammalian cells have transmembrane receptors that enable recognition of extracellular molecules and induce intracellular responses. The Notch receptor is an evolutionarily-conserved family of signaling receptors that utilize proteolytic cleavage to release extra- and intracellular domains in response to engagement with cognate ligands. The ability to undergo proteolytic cleavage is contained within a limited region of the Notch receptor, which contains the transmembrane domain and recognition sites for the cleavage event. The ability to undergo cleavage in response to ligand engagement is transferable, allowing the creation of synthetic receptors with a variety of ligand specificities which, upon binding, can release a variety of engineered extracellular and intracellular subdomains.

SUMMARY

The present disclosure provides a synthetic receptor comprising at least three domains. In certain aspects of the disclosure, the synthetic receptor may include: a) at least one domain comprising an extracellular domain configured to specifically bind to one or more ligands and to optionally release from the synthetic receptor after binding with said ligand, b) at least one domain comprising a transmembrane domain comprising or derived from a Notch receptor, and c) at least one domain comprising an intracellular domain configured to optionally initiate one or more functional activities when released from the synthetic receptor.

In some embodiments, upon binding an extracellular domain to a specific ligand, the synthetic receptor may undergo proteolytic cleavage to release either or both the extracellular domain and the intracellular domain. The extracellular binding domain may continue to bind to a cognate ligand and carry out one or more functional activities even if released. Functional activities can include at least one of antibody-dependent cellular cytotoxicity, complement-dependent cytotoxicity, apoptosis, or an enzymatic function. Further, by way of illustration and not limitation, the activity can be at least one of blockade or induction of protein-protein interactions or secretion of extracellular functional molecules. In some embodiments, extracellular functional molecules may be at least one of cytokines or chemokines.

The intracellular domain of the synthetic receptor may stimulate or inhibit one or more intracellular activities if released. In certain aspects of the disclosure, the intracellular domain is a secreted protein which stimulates or inhibits one or more extracellular activities if released.

These extracellular activities can include at least one of, but are not limited to, signaling, trafficking, adhesion, blockade of protein-protein interactions and/or stability. The one or more intracellular activities comprise at least one of signaling, gene expression, trafficking, and/or stability.

The extracellular domain may comprise an antibody or a fragment thereof. For example, in some embodiments, the extracellular domain may be a single chain variable fragment (scFV) molecule of an antibody that binds glycolipid disialoganglioside (GD2) fused to an Fc region of human IgG1.

The intracellular activity can also include at least one secreted fusion protein of a human CTLA4 extracellular domain fused to a wild type or modified Fc region of a human immunoglobulin G (IgG). In certain embodiments and by way of illustration, the human IgG may be at least one of IgG1, IgG2, or IgG4

The intracellular domain activity may also include at least one transgene of a human interleukin.

For example, in certain embodiments, the intracellular activity includes at least one transgene encoding human interleukin 2. In yet another embodiment, the at least one transgene may encode human interleukin 12. In some embodiments, the at least one transgene may encode any one of IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, IL-37, IL-38, IL-39, or IL-40.

In certain aspects of the disclosure, Notch receptor of the synthetic receptor can be a member of a human Notch receptor family. In other embodiments of the synthetic receptors, the Notch receptor is a member of the Notch receptor family from at least one of fly, worm, pig, or mouse.

The receptor may comprise a human CD3-specific single chain Fv molecule fused to an Fc region of a human IgG1. In these embodiments, the receptor may include a polypeptide sequence having at least 85%, at least 90%, at least 95%, or at least 98% amino acid sequence identity to SEQ ID NO: 1 or SEQ ID NO: 3. The receptor also may include a mouse CD3-specific single chain Fv molecule fused to an Fc region of a human IgG1. In these embodiments, the transgene comprises a polypeptide sequence having at least 85% amino acid sequence identity to SEQ ID NO: 3.

In some embodiments, the synthetic receptor also may comprise a single chain Fv molecule derived from dinutuximab fused to the Fc region of human IgG1. In these embodiments, the receptor comprises a polypeptide sequence having at least 85% amino acid sequence identity to SEQ ID NO: 2.

In some embodiments, the receptor further comprises a transgene encoding a fusion protein made of the human CTLA4 extracellular domain fused to the Fc region of human IgG1.

In certain other embodiments, the receptor further comprises a transgene encoding a human interleukin 2 molecule fused to the Fc region of human IgG1. In these embodiments, the transgene comprises a polypeptide sequence having at least 85% amino acid sequence identity to SEQ ID NO: 4.

In further embodiments, the receptor comprises a transgene encoding an engineered single chain human interleukin 12 molecule fused to the Fc region of human IgG1. In these embodiments, the transgene comprises a polypeptide sequence having at least 85% amino acid sequence identity to SEQ ID NO: 5.

A method of modulating an activity of a target cell using a synthetic receptor is also provided herein. The method may include contacting the synthetic receptor with a receptor on the target cell, allowing cleavage of the synthetic receptor while the extracellular binding domain remains bound to the target cell and releasing the intracellular domain into the nucleus where it induces expression of a gene. In some aspects of the disclosure, the extracellular domain may be an antibody or a fragment thereof. In certain embodiments, the extracellular domain also may be a single chain Fv molecule of an antibody that binds glycolipid disialoganglioside fused to an Fc region of human IgG1.

The intracellular activity of the method can include at least one fusion protein of a human CTLA4 extracellular domain fused to a wild type or modified Fc region of human IgG. In some embodiments, the IgG may comprises IgG1, IgG2, or IgG4. The intracellular activity also may include at least one transgene encoding a human interleukin. In some embodiments, the human interleukin is human IL2. In certain other embodiments, the intracellular activity includes at least one transgene encoding human IL12. In some embodiments, the at least one transgene may encode any one of IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, IL-37, IL-38, IL-39, or IL-40.

Contacting the synthetic receptor with a receptor on the target cell may comprise administering the synthetic receptor to a subject suffering from cancer. Contacting further may include administering the synthetic receptor to a subject suffering from an autoimmune disorder. Contacting further may include administering the synthetic receptor to a subject after an allotransplant or xenotransplant.

BRIEF DESCRIPTION OF THE DRAWINGS

FIG. 2A shows a synthetic receptor made of a human CD3-specific single chain Fv molecule fused to the Fc region of human IgG1. FIG. 2B illustrates a synthetic receptor made of a single chain Fv molecule derived from dinutuximab (sold under the trademark Unituxin® (dinutuximab) by United Therapeutics Corp.) fused to the Fc region of human IgG1. FIG. 2C shows a transgene encoding Belatacept, a fusion protein made of the human CTLA4 extracellular domain fused to the Fc region of human IgG1. FIG. 2D depicts a transgene encoding human interleukin 2 molecule fused to the Fc region of human IgG1. FIG. 2E shows a transgene encoding an engineered single chain human interleukin 12 molecule fused to the Fc region of human IgG1.

FIG. 5A graphically shows IL-2Fc production when pig aortic endothelial cells expressing the dinutuximab (sold under the trade mark Unituxin®) synthetic receptor are co-cultured with CHP-134 cells, which express the target glycolipid disialoganglioside (GD2) natively, for 48 hours. FIG. 5B graphically shows scIL-12Fc production level when pig aortic endothelial cells expressing the Unituxin synthetic receptor are co-cultured with CHP-134 cells, which express the target glycolipid disialoganglioside (GD2) natively, for 48 hours. IL-2Fc and scIL12-Fc protein levels were quantified by ELISA.

FIG. 6A graphically illustrates that the engineered human IL2-Fc protein encoded by the transgene functions at levels similar to native human IL2 in a CTLL-2 proliferation assay (relative fluorescence units). FIG. 6B shows results of a CTLL-2 proliferation assay wherein supernatants from porcine aortic endothelial cells engineered with the anti-GD2 synthetic receptor and a responsive transgene encoding human IL2-Fc cultured with or without human CHP-134 cells, which express the target glycolipid disialoganglioside (GD2) natively, for 48 hours. "Negative" refers to CTLL-2 cells alone and "Positive" refers to CTLL-2 cells cultured with purified human IL2-Fc protein.

FIG. 7 shows alignments of the transmembrane domain and flanking $1^{st}$ and $2^{nd}$ cleavage recognition sequences from Notch receptors of fly (dNotch) (SEQ ID NO: 6), worm (GLP-1) (SEQ ID NO: 7), pig (pNotch1) (SEQ ID NO: 8), mouse (mNotch1) (SEQ ID NO: 9) and human (hNotch1-4) (SEQ ID NOS 10-13, respectively, in order of appearance).

DETAILED DESCRIPTION

Definitions

Figure 1:
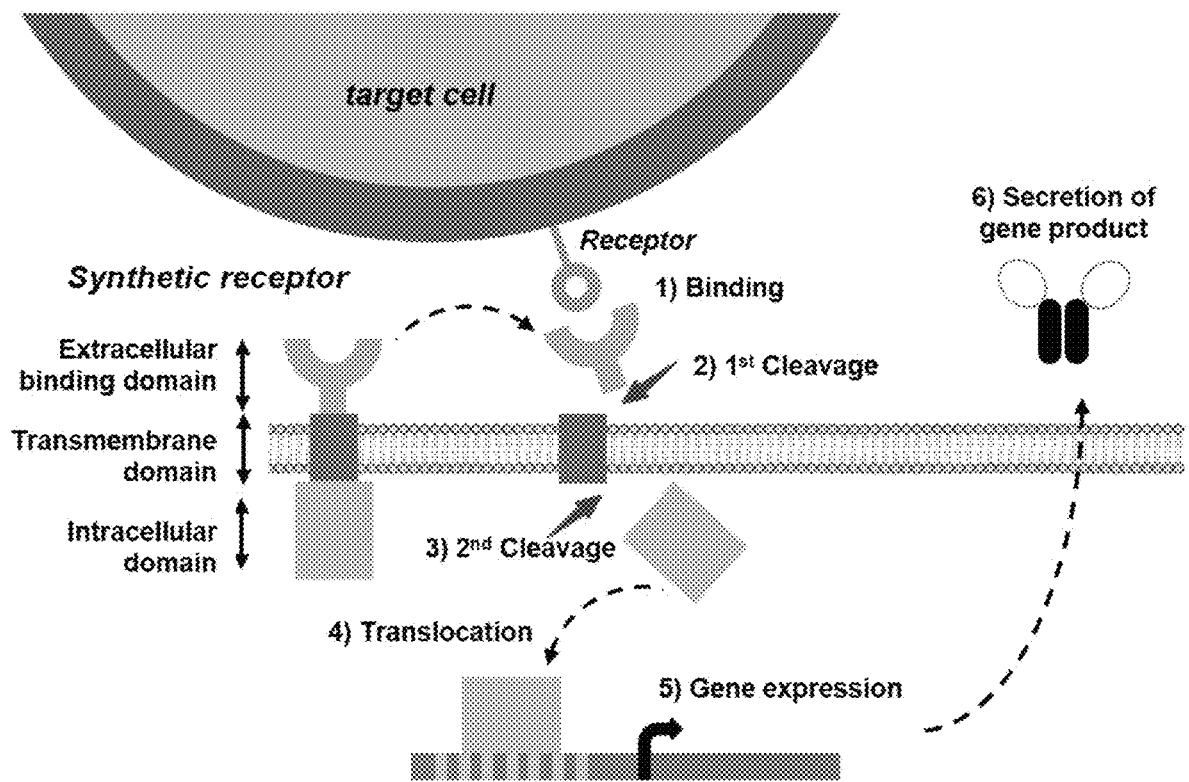
FIG. 1 illustrates a schematic diagram of a synthetic receptor of the present disclosure.

As used herein and in the appended claims, singular articles such as "a," "an," "the," and similar referents in the context of describing the elements are to be construed to cover both the singular and the plural, unless otherwise indicated herein or clearly contradicted by context.

As used herein, "about" is understood by persons of ordinary skill in the art and may vary to some extent depending upon the context in which it is used. If there are uses of the term which are not clear to persons of ordinary skill in the art given the context in which the term "about" is used, "about" will mean up to plus or minus 10% of the particular term.

As will be understood by one skilled in the art, for any and all purposes, all ranges disclosed herein also encompass any and all possible subranges and combinations of subranges thereof. Furthermore, as will be understood by one skilled in the art, a range includes each individual member.

The term "exemplary" as used herein refers to "serving as an example, instance, or illustration," and not "preferred" or "advantageous over other embodiments".

As used herein, "antibody-dependent cellular cytotoxicity" (ADCC), also referred to as antibody-dependent cell-mediated cytotoxicity, can refer to a mechanism of cell-mediated immune defense whereby an effector cell of an immune system actively lyses a target cell, whose membrane-surface antigens have been bound by specific antibodies. It is one of the mechanisms through which antibodies, as part of the humoral immune response, can act to limit and contain infection.

As used herein, "Belatacept" can refer to a soluble fusion protein, which links the extracellular domain of human cytotoxic T-lymphocyte-associated antigen 4 (CTLA4) to the modified Fc (hinge, CH2, and CH3 domains) portion of human immunoglobulin G1 (IgG1). Structurally, abatacept is a glycosylated fusion protein with a MALDI-MS molecular weight of 92,300 Da and it is a homodimer of two homologous polypeptide chains of 357 amino acids each. It is produced through recombinant DNA technology in mammalian CHO cells. The drug has activity as a selective co-stimulation modulator with inhibitory activity on T lymphocytes.

As used herein, "complement-dependent cytotoxicity" (CDC) can refer to an effector function of immunoglobulin, typically IgG and IgM antibodies. When they are bound to surface antigen on target cell (e.g., bacterial or viral infected cell), the classical complement pathway is triggered by bonding protein C1q to these antibodies, resulting in formation of a membrane attack complex (MAC) and target cell lysis.

As used herein, "dinutuximab" (sold under the trademark Unituxin® (dinutuximab) by United Therapeutics Corp.) is a GD2-binding monoclonal antibody indicated, in combination with granulocyte macrophage colony-stimulating factor (GM-CSF), interleukin-2 (IL-2), and 13-cis-retinoic acid (RA), for the treatment of pediatric patients with high-risk neuroblastoma who achieve at least a partial response to prior first-line multiagent, multimodality therapy.

As used herein, unless specified otherwise, "human interleukin" can refer to any one of IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, IL-37, IL-38, IL-39, or IL-40. Interleukin play essential roles in the activation and differentiation of immune cells, as well as proliferation, maturation, migration, and adhesion. They also have pro-inflammatory and anti-inflammatory properties.

Synthetic Receptors:

The synthetic receptors comprise a) at least one domain comprising an extracellular domain configured to specifically bind to one or more ligands and to optionally release from the synthetic receptor after binding with said ligand, b) at least one domain comprising a transmembrane domain derived from a Notch receptor, and c) at least one domain comprising an intracellular domain configured to optionally initiate one or more functional activities when released from the synthetic receptor.

In some embodiments, upon binding an extracellular domain to a specific ligand, the synthetic receptor may undergo proteolytic cleavage to release either or both the extracellular domain and the intracellular domain. The extracellular binding domain may continue to bind to a cognate ligand and carry out one or more functional activities even if released. Functional activities can include at least one of antibody-dependent cellular cytotoxicity, complement-dependent cytotoxicity, or an enzymatic function. The activity can be at least one of blockade or induction of protein-protein interactions or secretion of extracellular functional molecules. The antibody-dependent cellular cytotoxicity (ADCC), also referred to as antibody-dependent cell-mediated cytotoxicity, is a mechanism of cell-mediated immune defense whereby an effector cell of the immune system actively lyses a target cell, whose membrane-surface antigens have been bound by specific antibodies. It is one of the mechanisms through which antibodies, as part of the humoral immune response, can act to limit and contain infection. In some embodiments, extracellular functional molecules may be at least one of cytokines or chemokines.

The intracellular domain of the synthetic receptor may stimulate or inhibit one or more intracellular activities or extracellular activities, if released.

In certain aspects of the disclosure, the intracellular domain can be a secreted protein which stimulates or inhibits extracellular activity. These extracellular activities can include at least one of, but are not limited to, signaling, trafficking, adhesion, blockade of protein-protein interactions and/or stability. The one or more intracellular activities comprise at least one of signaling, gene expression, trafficking, and/or stability.

The extracellular domain may comprise an antibody or a fragment thereof. For example, in some embodiments, the extracellular domain may be a single chain Fv molecule of an antibody that binds glycolipid disialoganglioside (GD2) fused to an Fc region of human IgG1.

Figure 3:
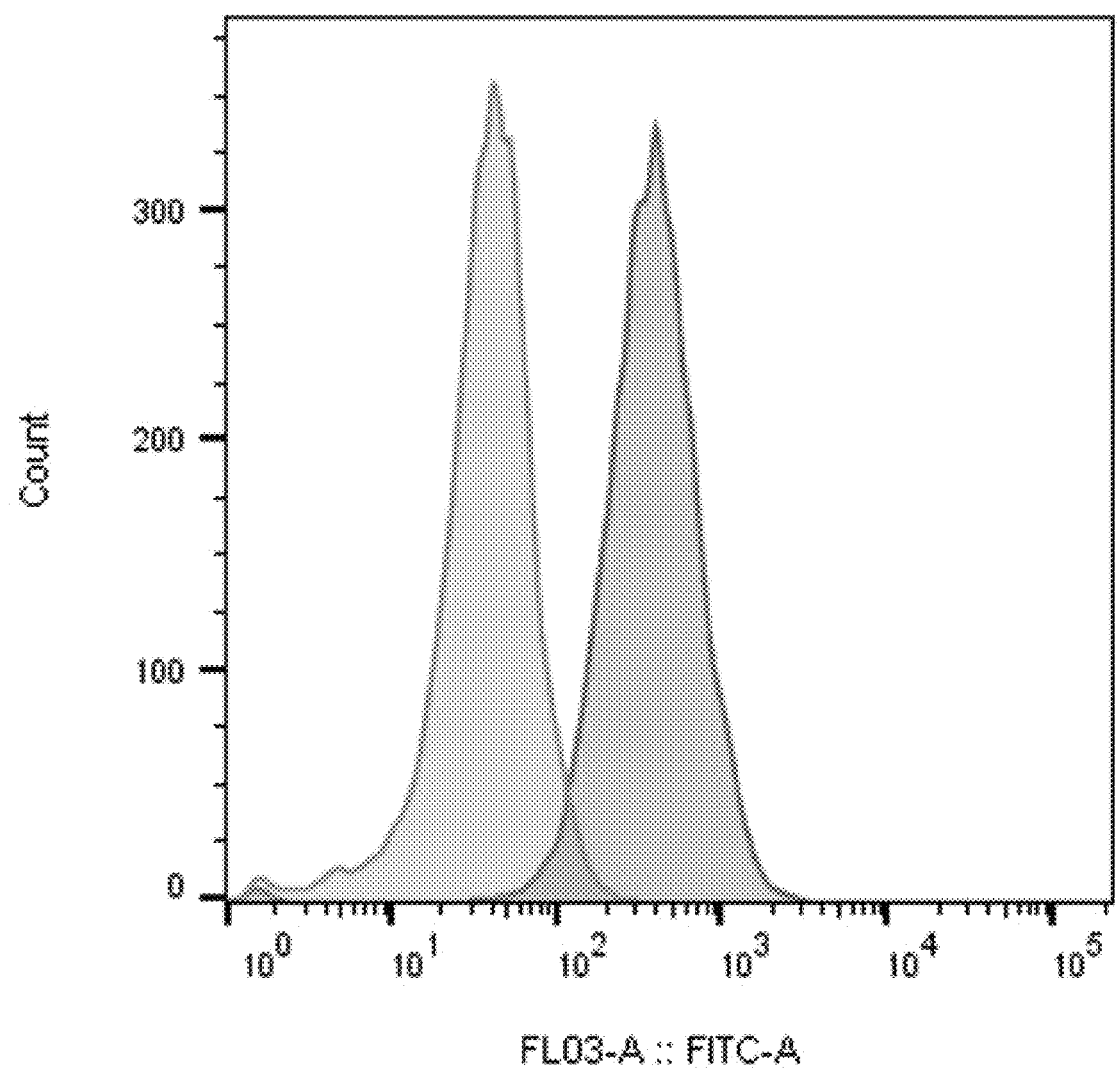
FIG. 3 graphically illustrates flow cytometric analysis demonstrating that the transgene-encoded Belatacept made of the human CTLA4 extracellular domain fused to the Fc region of human IgG1 binds to porcine CD80/CD86 molecules.

The intracellular activity can also include at least one secreted fusion protein of a human CTLA4 extracellular domain fused to a wild type or modified Fc region of a human immunoglobulin G (IgG). In certain embodiments and by way of illustration, the human IgG may be at least one of IgG1, IgG2, or IgG4. Referring to FIG. 3, a graphical depiction illustrates a flow cytometric analysis demonstrating that the transgene-encoded Betalacept made of human CTLA4 extracellular domain fused to the Fc region of human IgG1 binds to porcine CD80/CD86 molecules.

The intracellular domain activity may also include at least one transgene of a human interleukin.

For example, in certain embodiments, the intracellular activity includes at least one transgene encoding human interleukin 2. In yet another embodiment, the at least one transgene may encode human interleukin 12. In some embodiments, the at least one transgene may encode any one of IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, IL-37, IL-38, IL-39, or IL-40.

In certain aspects of the disclosure, Notch receptor subdomain of the synthetic receptor can be a member of the human Notch receptor family. In other embodiments of the synthetic receptors, the Notch receptor is a member of the Notch receptor family from at least one of fly, worm, pig, mouse, or human.

The receptor may comprise a human CD3-specific single chain Fv molecule fused to an Fc region of a human IgG1. In some embodiments, the receptor may include a polypeptide sequence having at least 85%, at least 90%, at least 95%, or at least 98% amino acid sequence identity to SEQ ID NO: 1, as disclosed in Table 1. The receptor may also comprise a mouse CD3-specific single chain Fv molecule fused to an Fc region of a human IgG1. In some embodiments, the receptor may include a polypeptide sequence having at least 85%, at least 90%, at least 95%, or at least 98% amino acid sequence identity to SEQ ID NO: 3, as disclosed in Table 3. Notch receptors may be derived from additional members of the human Notch receptor family (as shown in FIG. 7), or members of the Notch receptor family from other species which differ in sequence but retain the proteolytic cleavage functionality. FIG. 7 shows partial alignments of the first and second cleavage regions upon binding an extracellular domain to a specific ligand. Sequences from Notch receptors of fly (dNotch), worm (GLP-1), pig (pNotch1), mouse (mNotch1) and human (hNotch1-4) are shown.

In some embodiments, the synthetic receptor also may comprise a single chain Fv molecule derived from dinutuximab fused to the Fc region of human IgG1. In these embodiments, the receptor comprises a polypeptide sequence having at least 85%, at least 90%, at least 95%, or at least 98% amino acid sequence identity to SEQ ID NO: 2, as disclosed in Table 2.

In some embodiments, the receptor further comprises a transgene encoding a fusion protein made of the human CTLA4 extracellular domain fused to the Fc region of human IgG1.

In certain other embodiments, the receptor further comprises a transgene encoding a human interleukin 2 molecule fused to the Fc region of human IgG1. In these embodiments, the transgene comprises a polypeptide sequence having at least 85%, at least 90%, at least 95%, or at least 98% amino acid sequence identity to SEQ ID NO: 4, as disclosed in Table 4.

In further embodiments, the receptor comprises a transgene encoding an engineered single chain human interleukin 12 molecule fused to the Fc region of human IgG1. In these embodiments, the transgene comprises a polypeptide sequence having at least 85%, at least 90%, at least 95%, or at least 98% amino acid sequence identity to SEQ ID NO: 5, as disclosed in Table 5.

TABLE 1

Anti-CD3 hFc (SEQ ID NO: 1)

QVQLQQSGAELARPGASVKMSCKASGYTFTRYTMHWVKQRPGQGLEWIG
YINPSRGYTNYNQKFKDKATLTTDKSSSTAYMQLSSLTSEDSAVYYCAR
YYDDHYCLDYWGQGTTLTVSSGGGGSGGGGSGGGGSQIVLTQSPAIMSA
SPGEKVTMTCSASSSVSYMNWYQQKSGTSPKRWIYDTSKLASGVPAHFR
GSGSGTSYSLTISGMEAEDAATYYCQQWSSNPFTFGSGTKLEINRILDY
SFGGGAGRDIPPPLIEEACELPECQEDAGNKVCSLQCNNHACGWDGGDC
SLNFNDPWKNCTQSLQCWKYFSDGHCDSQCNSAGCLFDGFDCQRAEGQC
NPLYDQYCKDHFSDGHCDQGCNSAECEWDGLDCAEHVPERLAAGTLVVV
VLMPPEQLRNSSFHFLRELSRVLHTNVVFKRDAHGQQMIFPYYGREEEL
RKHPIKRAAEGWAAPDALLGQVKASLLPGGSEGGRRRRELDPMDVRGSI
VYLEIDNRQCVQASSQCFQSATDVAAFLGALASLGSLNIPYKIEAVQSE
TVEPPPPAQLHFMYVAAAAFVLLFFVGCGVLLSRKRRRQLCIQKLMSRL
DKSKVINSALELLNEVGIEGLTTRKLAQKLGVEQPTLYWHVKNKRALLD
ALAIEMLDRHHTHFCPLEGESWQDFLRNNAKSFRCALLSHRDGAKVHLG
TRPTEKQYETLENQLAFLCQQGFSLENALYALSAVGHFTLGCVLEDQEH
QVAKEERETPTTDSMPPLLRQAIELFDHQGAEPAFLFGLELIICGLEKQ
LKCESGGPADALDDFDLDMLPADALDDFDLDMLPADALDDFDLDMLPG

TABLE 2 dinutuximab hFc (SEQ ID NO: 2)

EVQLLQSGPELEKPGASVMISCKASGSSFTGYNMNWVRQNIGKSLEWIG
AIDPYYGGTSYNQKFKGRATLTVDKSSSTAYMHLKSLTSEDSAVYYCVS
GMEYWGQGTSVTVSSGGGGSGGGGSGGGGSDVVMTQTPLSLPVSLGDQA
SISCRSSQSLVHRNGNTYLHWYLQKPGQSPKLLIHKVSNRFSGVPDRFS

TABLE 2-continued dinutuximab hFc (SEQ ID NO: 2)

GSGSGTDFTLKISRVEAEDLGVYFCSQSTHVPPLTFGAGTKLELKRILD
YSFGGGAGRDIPPPLIEEACELPECQEDAGNKVCSLQCNNHACGWDGGD
CSLNFNDPWKNCTQSLQCWKYFSDGHCDSQCNSAGCLFDGFDCQRAEGQ
CNPLYDQYCKDHFSDGHCDQGCNSAECEWDGLDCAEHVPERLAAGTLVV
VVLMPPEQLRNSSFHFLRELSRVLHTNVVFKRDAHGQQMIFPYYGREEE
LRKHPIKRAAEGWAAPDALLGQVKASLLPGGSEGGRRRRELDPMDVRGS
IVYLEIDNRQCVQASSQCFQSATDVAAFLGALASLGSLNIPYKIEAVQS
ETVEPPPPAQLHFMYVAAAAFVLLFFVGCGVLLSRKRRRQLCIQKLMSR
LDKSKVINSALELLNEVGIEGLTTRKLAQKLGVEQPTLYWHVKNKRALL
DALAIEMLDRHHTHFCPLEGESWQDFLRNNAKSFRCALLSHRDGAKVHL
GTRPTEKQYETLENQLAFLCQQGFSLENALYALSAVGHFTLGCVLEDQE
HQVAKEERETPTTDSMPPLLRQAIELFDHQGAEPAFLFGLELIICGLEK
QLKCESGGPADALDDFDLDMLPADALDDFDLDMLPADALDDFDLDMLPG

TABLE 3 anti-CD3 mFc (SEQ ID NO: 3)

QVQLQQSGAELARPGASVKMSCKASGYTFTRYTMHWVKQRPGQGLEWIG
YINPSRGYTNYNQKFKDKATLTTDKSSSTAYMQLSSLTSEDSAVYYCAR
YYDDHYCLDYWGQGTTLTVSSGGGGSGGGGSGGGGSQIVLTQSPAIMSA
SPGEKVTMTCSASSSVSYMNWYQQKSGTSPKRWIYDTSKLASGVPAHFR
GSGSGTSYSLTISGMEAEDAATYYCQQWSSNPFTFGSGTKLEINRILDY
SFTGGAGRDIPPPQIEEACELPECQVDAGNKVCNLQCNNHACGWDGGDC
SLNFNDPWKNCTQSLQCWKYFSDGHCDSQCNSAGCLFDGFDCQLTEGQC
NPLYDQYCKDHFSDGHCDQGCNSAECEWDGLDCAEHVPERLAAGTLVLV
VLLPPDQLRNNSFHFLRELSHVLHTNVVFKRDAQGQQMIFPYYGHEEEL
RKHPIKRSTVGWATSSLLPGTSGGRQRRELDPMDIRGSIVYLEIDNRQC
VQSSSQCFQSATDVAAFLGALASLGSLNIPYKIEAVKSEPVEPPLPSQL
HLMYVAAAAFVLLFFVGCGVLLSRKRRRQLCIQKLMSRLDKSKVINSAL
ELLNEVGIEGLTTRKLAQKLGVEQPTLYWHVKNKRALLDALAIEMLDRH
HTHFCPLEGESWQDFLRNNAKSFRCALLSHRDGAKVHLGTRPTEKQYET
LENQLAFLCQQGFSLENALYALSAVGHFTLGCVLEDQEHQVAKEERETP
TTDSMPPLLRQAIELFDHQGAEPAFLFGLELIICGLEKQLKCESGGPAD
ALDDFDLDMLPADALDDFDLDMLPADALDDFDLDMLPG

TABLE 4

IL2-Fc (SEQ ID NO: 4)

APTSSSTKKTQLQLEHLLLDLQMILNGINNYKNPKLTRMLTFKFYMPKK
ATELKHLQCLEEELKPLEEVLNLAQSKNFHLRPRDLISNINVIVLELKG
SETTFMCEYADETATIVEFLNRWITFCQSIISTLTLTGGAEAAAKEAAAKE
AAAKAGGDKTHTCPPCPAPELLGGPSVFLFPPKPKDTLMISRTPEVTCV
VVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTK
NQVSLTCLVKGFYPSDIAVEWESNGQPENNYKTTPPVLDSDGSFFLYSK
LTVDKSRWQQGNVFSCSVMHEALHNHYTQKSLSLSPGK

TABLE 5 scIL12Fc (SEQ ID NO: 5)

IWELKKDVYVVELDWYPDAPGEMVVLTCDTPEEDGITWTLDQSSEVLGS
GKTLTIQVKEFGDAGQYTCHKGGEVLSHSLLLLHKKEDGIWSTDILKDQ
KEPKNKTFLRCEAKNYSGRFTCWWLTTISTDLTFSVKSSRGSSDPQGVT
CGAATLSAERVRGDNKEYEYSVECQEDSACPAAEESLPIEVMVDAVHKL
KYENYTSSFFIRDIIKPDPPKNLQLKPLKNSRQVEVSWEYPDTWSTPHS
YFSLTFCVQVQGKSKREKKDRVFTDKTSATVICRKNASISVRAQDRYYS
SSWSEWASVPCSGGGSGGGSGGGSGGGSRNLPVATPDPGMFPCLHEISQ
NLLRAVSNMLQKARQTLEFYPCTSEEIDHEDITKDKTSTVEACLPLELT
KNESCLNSRETSFITNGSCLASRKTSFMMALCLSSIYEDLKMYQVEFKT
MNAKLLMDPKRQIFLDQNMLAVIDELMQALNFNSETVPQKSSLEEPDFY
KTKIKLCILLHAFRIRAVTIDRVMSYLNASGGAEAAAKEAAAKEAAAKA
GGDKTHTCPPCPAPELLGGPSVFLEPPKPKDTLMISRTPEVTCVVVDVS
HEDPEVKFNWYVDGVEVHNAKTKPREEQYNSTYRVVSVLTVLHQDWLNG
KEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDK
SRWQQGNVFScSVMHEALHNHYTQKSLSLSPGK

Methods of Use and Treatment:

A method of modulating an activity of a target cell using a synthetic receptor is also provided herein. The method may include contacting the synthetic receptor with a receptor on the target cell, allowing cleavage of the synthetic receptor while the extracellular binding domain remains bound to the target cell and releasing the intracellular domain into the nucleus where it induces expression of a gene.

Referring to FIG. 1, a schematic diagram of a synthetic receptor of the present disclosure is provided, with reference to the possibility of a first proteolytic cleavage and a second cleavage after binding of a cognate ligand to the extracellular binding domain. Here, it is shown, in some embodiments, the synthetic receptor extracellular domain binds to a receptor on the target cell. This binding may induce cleavage of the synthetic receptor. The extracellular binding domain may remain bound to the target cell. The intracellular transcription activator domain may be released into the cytoplasm of the cell. The intracellular domain may then translocate into the nucleus, where it may induce expression of a gene, after which the gene product is secreted from the cell.

In some aspects of the disclosure, the extracellular domain may be an antibody or a fragment thereof. In certain embodiments, the extracellular domain also may be a single chain Fv molecule of an antibody that binds glycolipid disialoganglioside (GD2) fused to an Fc region of human IgG1.

The intracellular activity of the method can include at least one fusion protein of a human CTLA4 extracellular domain fused to a wild type or modified Fc region of human IgG. In some embodiments, the IgG may comprise IgG1, IgG2, or IgG4. The intracellular activity also may include at least one transgene encoding a human interleukin. In some embodiments, the human interleukin is human IL2. In certain other embodiments, the intracellular activity includes at least one transgene encoding human IL12. In some embodiments, the at least one transgene may encode any one of IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, IL-37, IL-38, IL-39, or IL-40.

Contacting the synthetic receptor with a receptor on the target cell may comprise administering the synthetic receptor to a subject suffering from cancer. Contacting further may include administering the synthetic receptor to a subject suffering from an autoimmune disorder. Contacting further may include administering the synthetic receptor to a subject after an allotransplant or xenotransplant.

Potential Applications:

The synthetic receptors of the present application include many potential applications. By way of illustration and not limitation, the synthetic receptors may serve in allotransplant and xenotransplant patients by recognizing alloantigens and xenoantigens and inducing a tolerogenic response. The receptors of the present disclosure may also act as therapeutics in oncology, recognizing tumor antigens and inducing an immunogenic response (i.e., immune activation). The receptors of the present disclosure also may be useful in regulating autoimmunity by recognizing pro-inflammatory or immune mediators and inducing an anti-inflammatory response (i.e., immune inhibition).

EXAMPLES

Example 1: Engineering Proof of Concept

Figure 2A:
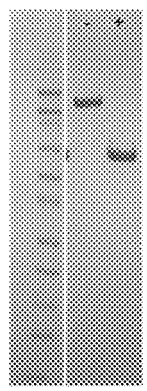
FIG. 2A-2E show results of polyacrylamide gel electrophoresis demonstrating the production of correctly-sized products from synthetic constructs.
Figure 2B:
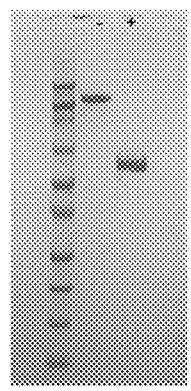
Figure 2C:
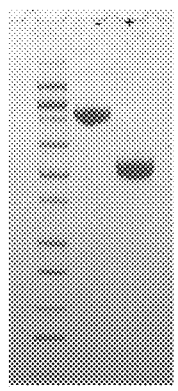
Figure 2D:
Figure 2E:
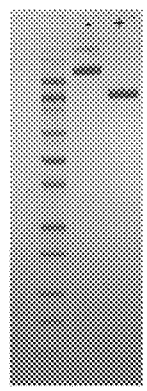

FIG. 2A-2E show results of a polyacrylamide gel electrophoresis demonstrating the production of correctly-sized products from synthetic constructs. FIG. 2A shows a synthetic receptor made of a human CD3-specific single chain Fv molecule fused to the Fc region of human IgG1. FIG. 2B illustrates a synthetic receptor made of a single chain Fv molecule derived from dinutuximab, sold under the trade mark Unituxin®, fused to the Fc region of human IgG1. FIG. 2C shows Belatacept, a fusion protein made of the human CTLA4 extracellular domain fused to the Fc region of human IgG1. FIG. 2D depicts human interleukin 2 fused to the Fc region of human IgG1. FIG. 2E shows an engineered single chain human interleukin 12 molecule fused to the Fc region of human IgG1.

Example 2: Anti-hCD3 Synthetic Receptor

Figure 4:
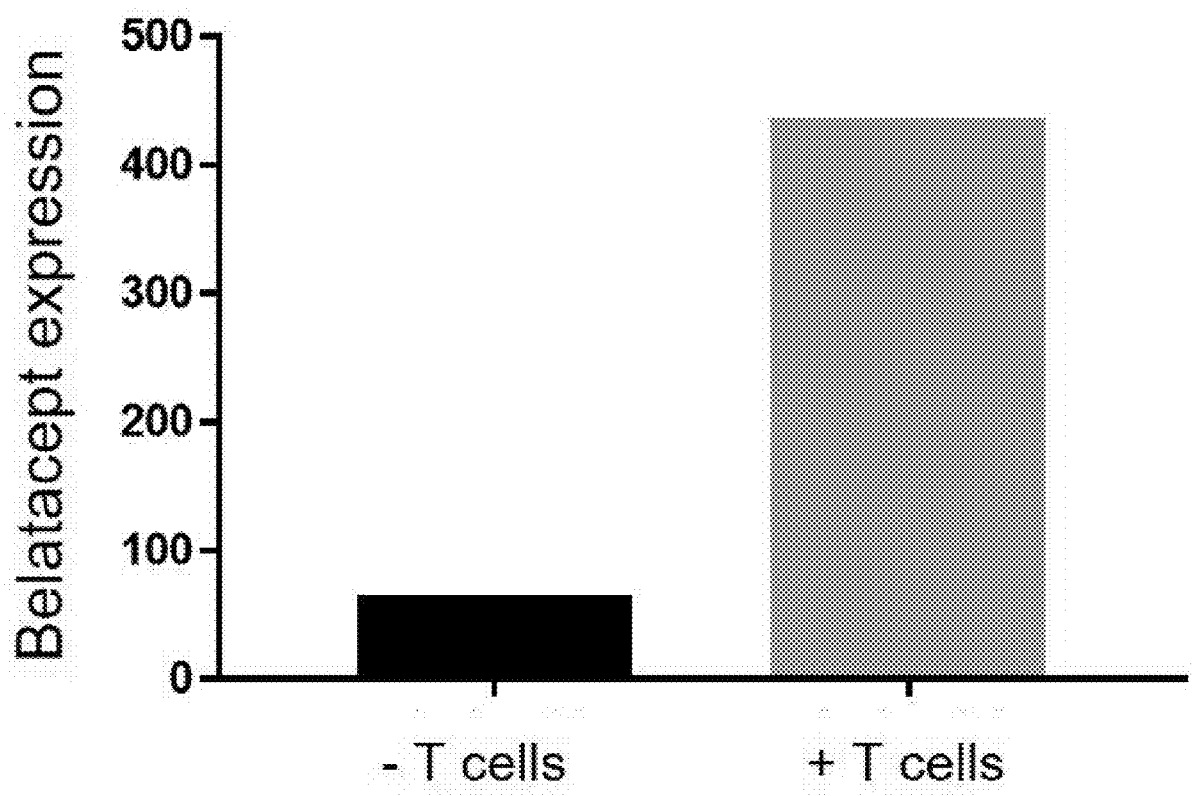
FIG. 4 graphically shows function of a synthetic receptor with extracellular domain made of a human CD3-specific single chain Fv molecule fused to the Fc region of human IgG1 which recognizes CD3 and responds with expression and secretion of Belatacept. Porcine aortic endothelial cells engineered with the anti-hCD3 synthetic receptor and a responsive transgene encoding Belatacept were exposed to human Jurkat T cells, which express CD3 natively, for 48 hours and analyzed for expression of Belatacept. Results show that only cells expressing the synthetic receptor induce expression of Belatacept in the presence of human T cells, which would have the dual benefit of blockade of CD3 and CD80/86.

Referring now to FIG. 4, results are shown for an assay for a synthetic receptor with extracellular domain capable of binding human CD3 and responding with the expression and secretion of Belatacept. Here, porcine aortic endothelial cells engineered with the anti-hCD3 synthetic receptor and a responsive transgene encoding Belatacept were exposed to human Jurkat T cells for forty-eight hours. The supernatant from the cells was collected and analyzed for expression of Belatacept. The synthetic receptor only induced expression of Belatacept in the presence of human T cells, which would have the dual benefit of blockade of CD3 and CD80/CD86.

Example 3: scFV Dinutuximab (Sold Under the Trade Mark Unituxin®) Fused with Fc-IgG1

Figure 5A:
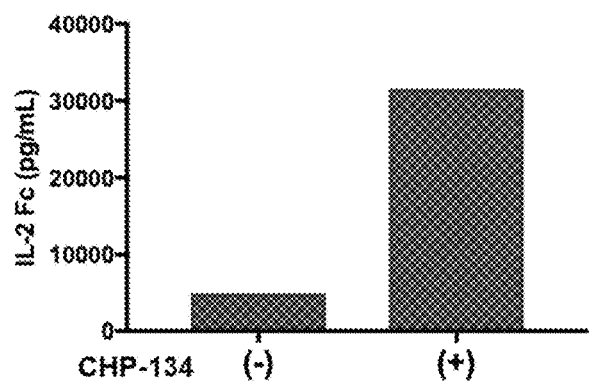
FIG. 5A-5B.
Figure 5B:
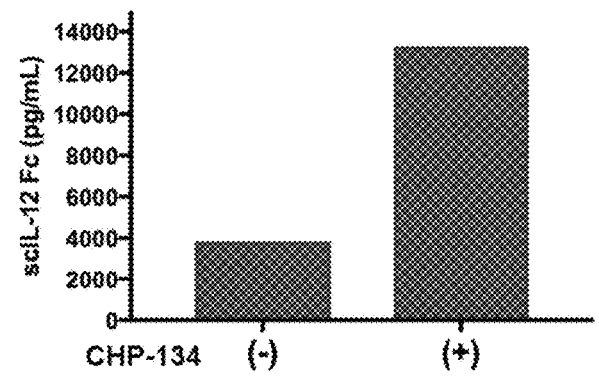

A synthetic receptor was created fusing a single chain Fv derived from dinutuximab with the Fc portion of an IgG1 antibody. This synthetic receptor binds to GD2 on tumor cells and responds with the expression and secretion of human TL-2Fc or human scIL-12Fc. Porcine aortic endothelial cells engineered with the anti-GD2 synthetic receptor and a responsive transgene encoding human IL-2Fc or human scIL-12Fc were exposed to human CHP134 cells for 48 hours. The supernatant from the cells was collected and analyzed for expression of human IL-2Fc or human scIL-12Fc. FIG. 5A and FIG. 5B show the results of the protocol, with IL-2Fc graphically depicted in FIG. 5A and scIL-12Fc graphically depicted in FIG. 5B. The synthetic receptor only induces expression of human IL2-Fc or human scIL12-Fc in the presence of GD2-expressing CHP-134 cells, which would have the dual benefit of blockade of GD2 and production of anti-tumor cytokines.

Example 4: CTLL-2 Proliferation Assay

Figure 6A:
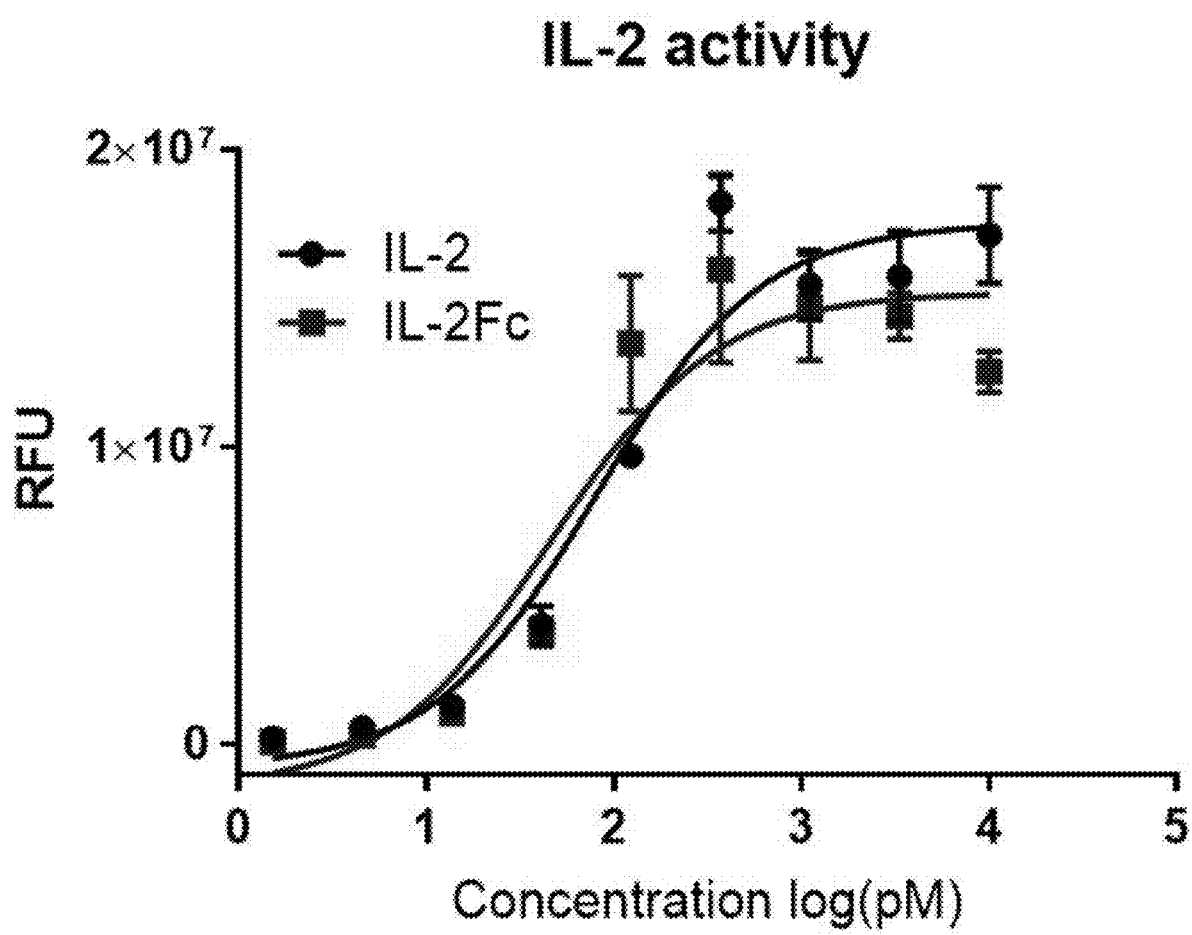
FIG. 6A-6B.
Figure 6B:
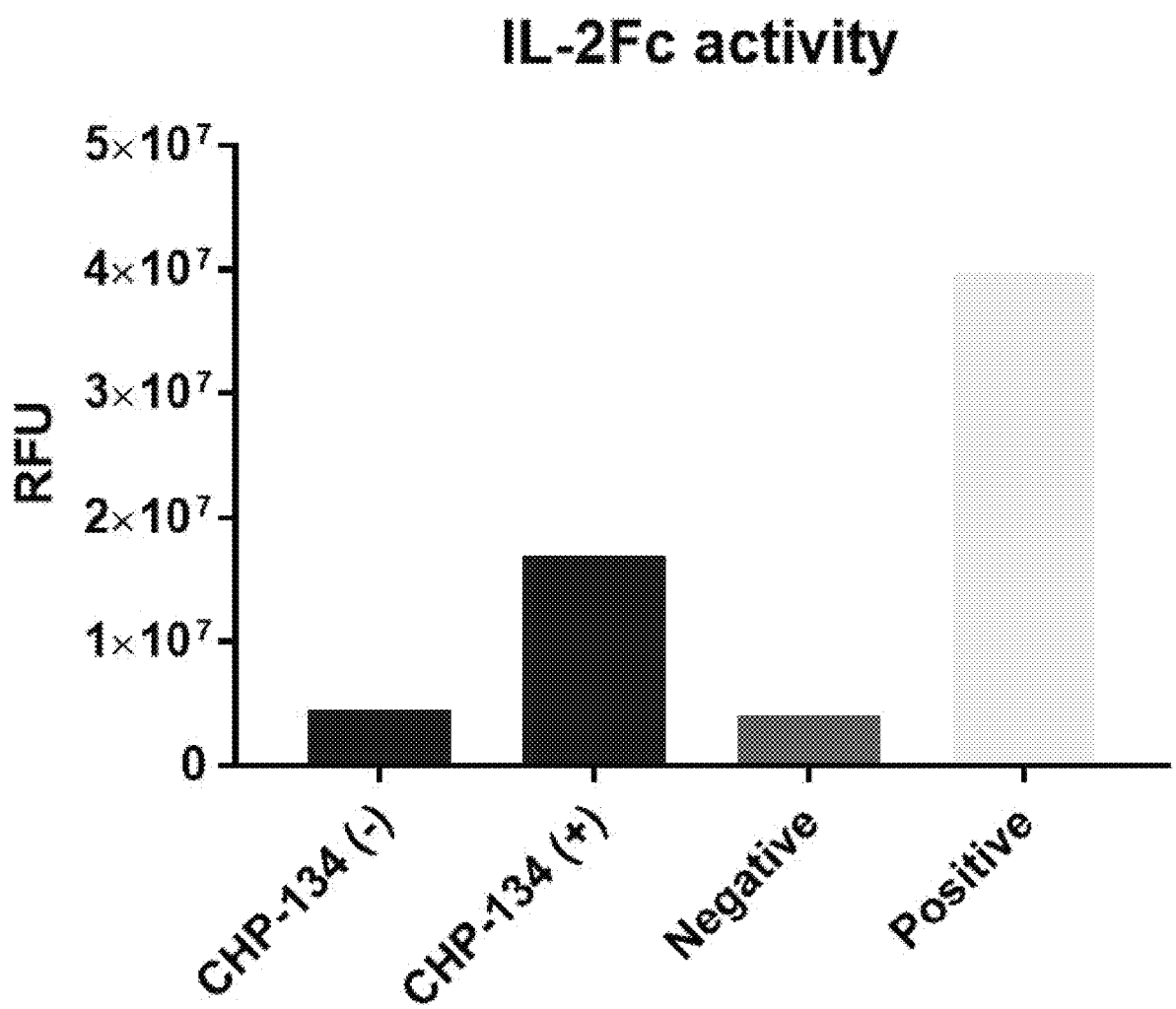

CTLL is a subclone of T cells derived from a C57BL/6 mouse. The cells require IL-2 for growth and are used to assay for its presence in conditioned media and thus may be used to determine the presence of T-cell cytokines by measuring the proliferation of the CTLL-2 cells. In this example, supernatants from porcine aortic endothelial cells engineered with an anti-GD2 synthetic receptor and a responsive transgene encoding human IL-2Fc co-cultured with or without human CHP-134 cells were tested for 48 hours in a CTLL-2 proliferation assay. Results of the assay are shown in FIG. 6A and FIG. 6B. FIG. 6A graphically illustrates that purified engineered human IL2-Fc protein encoded by the transgene functions at levels similar to native human IL2 in a CTLL-2 proliferation assay (RFU refers to relative fluorescence units). FIG. 6B shows IL-2-Fc activity in the CTLL-2 proliferation assay. FIG. 6B graphically illustrates the results of porcine aortic endothelial cells engineered with the anti-GD2 synthetic receptor and a responsive transgene encoding human IL2-Fc cultured for 48 hours with or without GD2-expressing CHP134 cells. In FIG. 6B, CHP-134 (−) refers to culture without CHP-134 cells and CHP-134(+) refers to culture with CHP-134 cells. "Negative" refers to CTLL-2 cells alone and "Positive" refers to CTLL-2 cells plus purified human IL2-Fc protein. As shown in FIG. 6B, the synthetic receptor only induced expression of IL2-Fc in co-cultures with GD2-expressing human CHP-134 cells, as shown by the ability of the CHP-134 supernatant to stimulate CTLL-2 proliferation.

EQUIVALENTS

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control. The attached Appendix is incorporated herein by reference.

We claim:

1. A modular synthetic receptor comprising:
    a) an extracellular domain configured to specifically bind to one or more ligands and to optionally release from the synthetic receptor after binding with said ligand,
    b) a transmembrane domain derived from a Notch receptor, and
    c) an intracellular domain configured to optionally initiate a functional activity when released from the synthetic receptor,
    wherein the extracellular domain comprises (i) a human CD3-specific single chain Fv molecule fused to the Fc region of human IgG1 or (ii) a single chain Fv molecule derived from dinutuximab fused to the Fc region of human IgG1.

2. The synthetic receptor of claim 1, wherein upon binding the extracellular domain to a specific ligand, the synthetic receptor undergoes proteolytic cleavage to release either or both the extracellular domain and the intracellular domain.

3. The synthetic receptor of claim 1, wherein the extracellular domain continues to bind to a cognate ligand and carry out one or more functional activities even if released.

4. The synthetic receptor of claim 1, wherein the functional activities comprise at least one of antibody-dependent cellular cytotoxicity or complement-dependent cytotoxicity complement-dependent cytotoxicity, or an enzymatic function.

5. The synthetic receptor of claim 1, wherein the intracellular domain stimulates or inhibits one or more intracellular activities if released.

6. The synthetic receptor of claim 1, wherein the intracellular domain comprises at least one secreted fusion protein of a human CTLA4 extracellular domain fused to a wild type or modified Fc region of a human immunoglobulin G (IgG).

7. The synthetic receptor of claim 6, wherein the human IgG comprises IgG1, IgG2, or IgG4.

8. The synthetic receptor of claim 1, wherein the intracellular domain comprises at least one transgene of a human interleukin.

9. The synthetic receptor of claim 5, wherein the intracellular domain comprises at least one transgene encoding human interleukin 2.

10. The synthetic receptor of claim 5, wherein the intracellular domain comprises at least one transgene encoding human interleukin 12.

11. The synthetic receptor of claim 1, wherein the Notch receptor is a member of the human Notch receptor family.

12. The synthetic receptor of claim 1, wherein the Notch receptor is a member of the Notch receptor family from at least one of fly, worm, pig, mouse or human.

13. The synthetic receptor of claim 1, wherein the receptor further comprises a transgene encoding a fusion protein made of the human CTLA4 extracellular domain fused to the Fc region of human IgG1.

14. The synthetic receptor of claim 1, wherein the receptor further comprises a transgene encoding a human interleukin 2 molecule fused to the Fc region of human IgG1.

15. The synthetic receptor of claim 1, wherein the synthetic receptor comprises the human CD3-specific single chain Fv molecule fused to the Fc region of human IgG1.

16. The synthetic receptor of claim 1, wherein the synthetic receptor comprises the single chain Fv molecule derived from dinutuximab fused to the Fc region of human IgG1.

* * * * *